United States Patent
Zilberman et al.

(10) Patent No.: US 8,299,149 B2
(45) Date of Patent: Oct. 30, 2012

(54) WATER MISCIBLE SOLVENT BASED PROCESS FOR PURIFYING A BISPHOSPHATE

(75) Inventors: Joseph Zilberman, Haifa (IL); Dorit Canfi, Zichron Yaacov (IL); Andrew Gregor, Hopewell Junction, NY (US); Andrew Piotrowski, Yorktown Heights, NY (US)

(73) Assignee: ICL-IP America Inc., Ardsley, NY (US)

( * ) Notice: Subject to any disclaimer, the term of this patent is extended or adjusted under 35 U.S.C. 154(b) by 0 days.

(21) Appl. No.: 13/133,346

(22) PCT Filed: Dec. 21, 2009

(86) PCT No.: PCT/US2009/068975
§ 371 (c)(1),
(2), (4) Date: Jul. 29, 2011

(87) PCT Pub. No.: WO2010/075276
PCT Pub. Date: Jul. 1, 2010

(65) Prior Publication Data
US 2012/0022193 A1    Jan. 26, 2012

(51) Int. Cl.
*C08K 5/523* (2006.01)
(52) U.S. Cl. ................................................ 524/127
(58) Field of Classification Search .................. 524/117, 524/127
See application file for complete search history.

(56) References Cited

U.S. PATENT DOCUMENTS

| | | |
|---|---|---|
| 3,356,775 A | 12/1967 | Mitchell et al. |
| 5,097,056 A | 3/1992 | Segall et al. |
| 5,457,221 A | 10/1995 | Brady et al. |
| RE36,188 E | 4/1999 | Gosens et al. |
| 6,727,301 B1 | 4/2004 | Eckel et al. |
| 6,753,366 B1 | 6/2004 | Eckel et al. |
| 2003/0171463 A1* | 9/2003 | Weinberg et al. ............ 524/115 |

FOREIGN PATENT DOCUMENTS

| | | |
|---|---|---|
| EP | 0690063 B1 | 8/2001 |
| EP | 1327635 B1 | 8/2005 |
| JP | 08176163 | 7/1996 |
| JP | 09192506 | 7/1997 |
| JP | 10310593 | 11/1998 |
| WO | WO98/35970 | 8/1998 |
| WO | WO2008/027536 A1 | 3/2008 |

OTHER PUBLICATIONS

Notification of Transmittal of the International Search Report and The Written Opinion of the International Searching Authority, (Form PCT/ISA/220—3pages),(Form PCT/ISA/210—4 pages), (Form PCT/ISA/237—6 pages).

* cited by examiner

*Primary Examiner* — Peter Szekely
(74) *Attorney, Agent, or Firm* — Dilworth & Barrese LLP

(57) ABSTRACT

There is provided herein a process for purifying bisphosphate comprising solvating a molten bisphosphate in a mixture of water and water miscible solvent; cooling the solution over a period and to a temperature that provides for crystallization of solid product; increasing the pH of the solution prior to, and/or during, and/or after the initiation of crystallization, and/or after crystallization, by the addition of a base; and after crystallization is complete, separating solid product from the solution; washing the separated solid product in the same and/or different mixture of water and water miscible solvent; and, washing the solid product which has been washed in the mixture with water.

11 Claims, No Drawings

WATER MISCIBLE SOLVENT BASED PROCESS FOR PURIFYING A BISPHOSPHATE

FIELD OF THE INVENTION

The present invention relates to a process of purifying phosphates, e.g, solid bisphosphates, and more particularly, to a process for making solid, powdered phenylphosphate esters of hydroquinone, with low acid value and low contents of organic impurities, residual catalyst and alkaline metals.

BACKGROUND OF THE INVENTION

Phosphorus based flame retardants can be used for flame retarding engineering plastics like PC/ABS, ABS, HIPS and modified HIPS. Crude phosphate products have been heretofore purified by dissolving the phosphate in non-water miscible solvents such as toluene, heptane, xylenes or dibutyl ether, and then subjecting the non-water miscible solvent/product solution to a series of hot aqueous washes. The typical wash procedure includes acid washes to remove the catalyst.

Examples of these routes are described in European Patent Application Publication No. 690063 and Japanese Patent Publications Nos. 98310593, 09192506 and 08176163. However, any such treatment is followed by multiple water washings to remove slight amounts of acids or alkaline metals salts remaining in the phenylphosphate esters after the phase separation.

WO 98/35970 teaches that liquid arylphosphate esters can be used without any purification to remove the $MgCl_2$ catalyst. However, this approach overlooks corrosion problems originating from $Cl^-$ remaining in the product.

The multiple aqueous wash solutions physically separated from the non-water miscible solvent/product solution which are mentioned above, have to be disposed of creating considerable aqueous waste with a relatively high content of organics. It would be desirable to develop a less complex process which reduces the amount of aqueous waste and organics generated in this liquid/liquid extraction process of purifying phosphates without compromising the yield and quality.

SUMMARY OF THE INVENTION

The increased acidity of the some bisphosphates previous to the invention herein, may cause hydrolytic instability when it is formulated in a polycarbonate/acrylonitrile-butadiene-styrene blend. In general, in order to reduce the content of acidic phosphorus-containing impurities in arylphosphates, neutralization wash with an alkaline metal hydroxide, or other basic compounds is carried out, followed by multiple water washes which are often accompanied by the undesirable formation of emulsions.

The present invention overcomes the problems of the prior art by providing a simple and convenient process for preparing solid, powdered bisphosphates with low acid value and low contents of organic impurities, residual catalyst and alkaline metals, wherein neither acid nor alkaline washing are required.

Accordingly, the invention herein is directed to a simplified process of purifying bisphosphate compounds, preferably solid bisphosphate compounds, which eliminates the need for non-water miscible solvent, avoids the excessive amounts of aqueous waste, and the formation of emulsions as compared with previously known purification processes, while providing a high purity product.

There is provided in one embodiment herein a process for purifying bisphosphate comprising a process for purifying bisphosphate comprising: solvating a molten bisphosphate in a mixture of water and water miscible solvent; cooling the solution over a period and to a temperature that provides for crystallization of solid product; increasing the pH of the solution prior to, and/or during, and/or after the initiation of crystallization, and/or after crystallization of the product is complete, by the addition of a base; and after crystallization is complete, separating solid product from the solution; washing the separated solid product in the same and/or different mixture of water and water miscible solvent; and, washing the solid product which has been washed in the mixture of water and water miscible solvent, with water.

DETAILED DESCRIPTION OF THE INVENTION

The invention herein is directed to a simplified process of purifying bisphosphate compounds, which eliminates the need for toluene and like compounds, such as xylenes, hexane, heptane, dibutyl ether and the like, and avoids the excessive aqueous waste product, as compared with previously known purification processes.

This invention in one non-limiting embodiment relates to a novel process for purifying bisphosphates using a solution of a water miscible solvent (for example, water miscible alcohol such as water miscible primary and secondary alcohol) and water with a base. Specifically, in one non-limiting embodiment this invention pertains to the purification of Hydroquinone bis(diphenyl phosphate) (HDP) using a n-propanol/water solution with sodium hydroxide. Prior to this time, hydroquinone bis(diphenyl phosphate) has been purified by the above described process using the non-water miscible solvent such as toluene.

HDP is a solid halogen free, phosphorus based flame retardant intended for engineering resins such as PC/ABS, V2-ABS, modified PPO and FR-styrenic composites.

The process herein results in similar yields and product quality to the previously known non-water miscible solvent process with an added benefit of significant reduction in waste. In addition, the present process prevents the undesirable formation of emulsions which were described above.

It will be understood herein that the term "bisphosphate" comprises any bisphosphates which are described in WO 2008027536 (A1) the contents of which are incorporated by reference herein in their entirety, and any phosphates described herein.

The present invention is directed to bisphosphates and resin compositions containing the same. The present invention can be used for purification of any solid bisphosphates. Solid bisphosphate is understood to be a solid bisphosphate with a melting point above 30 degrees Celsius, preferably above 40 degrees Celsius, more preferably above 80 degrees Celsius and most preferably above 100 degrees Celsius. The purified bisphosphate can have the same ranges of melting points.

The bisphosphates that can be used in the process herein can be crude bisphosphate products made by the process described in WO 2008027536 (A1). In one embodiment wherein the bisphosphate is of the general formula (I):

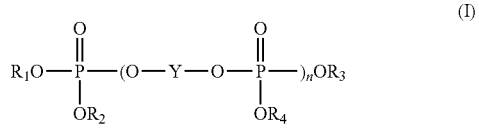

wherein $R_1$, $R_2$, $R_3$ and $R_4$ each independently is alkyl, aryl, alkaryl or arylalkyl containing up to about 30 carbon atoms, preferably up to 20 carbon atoms, and most preferably up to about 12 carbon atoms, optionally interrupted with heteroatoms, Y is a divalent organic group such as a divalent alkyl, aryl, alkaryl, arylalkyl or diaryl group containing up to about 20 carbon atoms, preferably up to about 16 carbon atoms and most preferably up to about 12 carbon atoms, or a divalent alkylene group of up to about 12 carbon atoms, and n has an average value of from about 1.0 to about 1.4, preferably from about 1.0 to less than or equal to about 1.2, and more preferably from about 1.0 to about 1.1. Heteroatoms can comprise halogen, oxygen, nitrogen and sulfur. In one embodiment each of $R_1$, $R_2$, $R_3$ and $R_4$ are phenyl. In one embodiment Y is a divalent phenyl group, so that the molecule is a hydroquinone bisphosphate. Y can also comprise a divalent alkylene group containing up to about 12 carbon atoms, preferably up to 8 carbon atoms, e.g., ethylene, propylene, isopropylene and the like.

In one embodiment the bisphosphate is of the general formula (I), and is other than biphenol bis(diphenyl phosphate), e.g., other than 4,4-biphenol his (diphenyl phosphate).

In one embodiment herein, the present invention is directed to oligomeric hydroquinone bisphosphate flame retardants having the structure of formula (I), wherein preferably $R_1$, $R_2$, $R_3$ and $R_4$ each independently is a phenyl group of general formula (II):

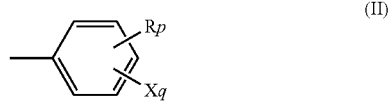

wherein each R independently is alkyl of 1 to 4 carbon atoms, each X independently is chlorine or bromine, p is 0 to 3 and q is 0 to 5 with the sum of p and q being 0 to 5 and n has an average value of from about 1.0 to about 1.4, preferably from about 1.0 to less than or equal to about 1.2, and more preferably from about 1.0 to about 1.1. A particularly preferred oligomeric bisphosphate within formula (I) above is hydroquinone bis-(diphenylphosphate) (HDP), i.e., $R_1$, $R_2$, $R_3$ and $R_4$ are each phenyl.

In general, the hydroquinone bis-phosphates of the present invention are prepared by reacting a diaryl halophosphate with hydroquinone in the presence of a catalyst. In a preferred embodiment of the invention, diphenylchlorophosphate (DPCP) is reacted with hydroquinone in the presence of $MgCl_2$ to produce hydroquinone bis-(diphenylphosphate). In accordance with the present invention, hydroquinone bis (diphenylphosphate) within general formula (I) prepared by this process can preferably have an average n value from about 1.0 to about 1.4, more preferably from about 1.0 to about 1.2 and most preferably from 1.0 to about 1.1.

In another embodiment, the hydroquinone bisphosphates of the present invention are prepared by reacting hydroquinone with a reaction mixture comprising a diarylhalophosphate (such as diphenylchlorophosphate) and a monoaryldihalophosphate (such as monophenyl dichlorophosphate (MPCP)) in the presence of a catalyst, such as $MgCl_2$. A process such as this is described in U.S. Pat. No. 5,457,221, the entire contents of which are incorporated by reference herein. In accordance with the present invention, hydroquinone bisphosphates within general formula (I) prepared by this process will have an average n value of from about 1.0 to about 1.4, preferably 1.0 to about 1.2, and most preferably 1.0 to about 1.1

In another embodiment herein the hydroquinone bisphosphates of the present invention with an average n of 1.0-1.4, preferably 1.0-1.2, more preferably 1.0-1.1 are prepared by a reverse route starting from hydroquinone (HQ) and $POCl_3$ followed by reaction with phenol.

Scheme 1 Preparation of oligomeric hydroquinone bisphosphates from hydroquinone and phosphorus oxychloride

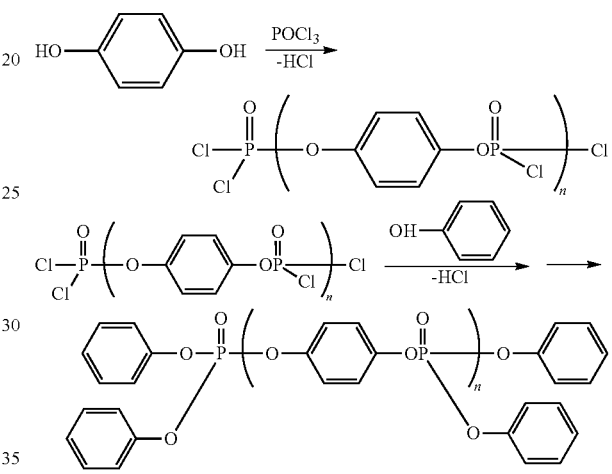

This route comprises a first step in which HQ is reacted with $POCl_3$ in the presence of a Lewis acid catalyst, and a second step in which the resulting intermediate phosphorochloridate is reacted with excess phenol. Among the suitable Lewis acid catalysts are aluminium chloride, titanium tetrachloride, and preferably, magnesium chloride. The amount of $MgCl_2$ used is from 0.001 to 0.01 mol per 1 mol of HQ, and more preferably from 0.002 to 0.004 mol, based on 1 mol HQ.

In the first step, mixtures with the desired distribution of monomer and higher oligomers can be produced, depending on the particular ratio of $POCl_3$ and HQ. One skilled in the art will recognize that the greater the excess of $POCl_3$, the higher will be the concentration of monomeric diphosphorotetrachloridate compared to oligomers. The amount of $POCl_3$ used should be more than 3.8 mol per 1 mol HQ in order to obtain a phenylphosphate ester with a monomer content above 75%. A ratio of more than 5 mol $POCl_3$ with respect to 1 mol of HQ is preferable when a product is desired with a monomer content of above 85%. Using a molar ratio greater than 6 is inexpedient due to the need to distill and recycle the larger quantities of $POCl_3$. When the monomer content in the phosphate esters is below about 65% it becomes difficult to carry out the purification according to the method of the present invention.

The reaction of HQ with phosphorus oxychloride ($POCl_3$) (first step) is carried out at a temperature from 90 to 125° C., and preferably from 95 to 120° C., and is continued until the conversion of the HQ is complete. It is critical to remove any unreacted $POCl_3$ before adding phenol, in order to minimize the formation of triphenyl phosphate. The excess $POCl_3$ is fully stripped at 100-150° C., and preferably at 115-125° C., under vacuum which is gradually applied until the pressure is about 20 torr.

In order to attain full conversion of the phosphorochloridates in the reaction of the intermediate phosphorochloridate with excess phenol (second step), the amount of phenol used is about 4 moles, based on 1 mol HQ. An increase of the ratio to above four is inexpedient due to the need to distill and recycle the larger quantities of phenol. Said second step is carried out in the presence of the same catalyst as in the first step, at a temperature of from 120 to 180° C., and preferably between 130-160° C. At the end of the reaction a vacuum of 20-300 torr is applied to lead the reaction to completion by driving off the hydrogen chloride formed. Subsequently, the unreacted phenol is removed by sparging with an inert gas such as nitrogen or argon, at 140-170° C., and more preferably at 155-160° C., in combination with vacuum or without it, in order to bring the phenol remaining in the crude phenylphosphate ester to a level of less than 0.5%, and preferably to less than 0.3%.

In one preferred embodiment of the invention, high purity (99%) diphenylchlorophosphate (DPCP) is reacted with hydroquinone to yield essentially pure monomeric bisphosphate, i.e. average n value of about 1.02. The relatively pure monomeric bisphosphate has a higher melting point than oligomers prepared from less pure DPCP and provides for a free-flowing powder product.

Typically, the value of n in formula (I) is calculated by firstly determining the proportions of oligomeric phosphate species (oligophosphates) in the product by high pressure liquid chromatography (HPLC) measurements. The weight average (n) value is then determined (calculated) in known manner from the proportions of the oligophosphates. In calculating the value of n, monophosphate species, e.g. triphenylphosphate, may or may not be included in the calculation. The n values ascribed to the oligomeric bis-phosphates of the present invention were calculated omitting the monophosphate species in the calculation. However, if the monophosphate species are considered (used) in the calculation, lower n values, depending on the amount of monophosphate species present, may result.

In one embodiment herein the mixture of water and water miscible solvent is a mixture of water and at least one water miscible solvent selected from the group consisting of methanol, ethanol, n-propanol, isopropanol, monomethyl ether of ethylene glycol, monoethyl ether of ethylene glycol, THF, dioxane, acetone, acetonitrile, dimethyl ether of ethylene glycol and mixtures of any two or more of the foregoing. In one embodiment the mixture can comprise two or more water miscible solvents. In one embodiment herein the water miscible solvent can comprise a water miscible alcohol containing from 1 to 4 carbon atoms, preferably from 1 to 3 carbon atoms, e.g., a primary or secondary alcohol. Most preferred are ethanol, isopropanol and n-propanol, with isopropanol and n-propanol being the solvents of choice. Propanols are relatively inexpensive and are easily recovered by simple azeotropic distillation techniques for recycle, thus significantly reducing the amount of aqueous waste generated in the purification process. Since there is a large water presence in the processes of this invention, it is not necessary to recover the alcohol with a low water content, thus lowering the alcohol recovery cost and reducing, due to the azeotropic distillation, the amount of aqueous waste generated in the purification process.

In one embodiment herein "water miscible" in the expression "water miscible solvent" is well understood by those skilled in the art, but can specifically herein refer to any solvent that can be homogenously solvated, (i.e., with no phase separation present in the water miscible solvent and water mixture) in water. The water miscible solvent of the present invention is a solvent which, in the prescribed amount, is capable of dissolving the crude bisphosphate at an elevated temperature, and which does not separate from the water in the solvent—water mixture. An elevated temperature can comprise above 30 degrees Celsius, preferably above 50 degrees Celsius, more preferably about 80 degrees Celsius and most preferably above 100 degrees Celsius.

The water miscible solvent herein in one non-limiting embodiment is understood to be an inert solvent.

In one embodiment herein the water can comprise at least one of tap water, deionized water, distilled water and nanopure water.

In another embodiment herein the molten bisphosphate is melted at a temperature of from 100 degrees Celsius to about 130 degrees Celsius, preferably from about 105 to about 120 degrees and most preferably from about 106 to about 108 degrees Celsius.

In one embodiment herein the molten bisphosphate can be solvated at the temperature it is at when melted, or the molten bisphosphate can be allowed to cool to a lower temperature provided it is in a completely molten state when contacted with the mixture of water and water miscible solvent. Alternatively the bisphosphate can be in the solid form and then solvated in the water miscible solvent by increasing the temperature; and it will be understood herein that any embodiments directed herein to a molten bisphosphate can be adapted herein to a solid bisphosphate which is then solvated in the water miscible solvent by increasing the temperature. In one embodiment herein the mixture of water and water miscible solvent comprises a mixture of water miscible solvent to water of from about 1:99 to about 99:1 volume percent, based on the total volume of the mixture, preferably about 10:90 to about 90:10 volume percent, based on the total volume of the mixture, more preferably from about 20:80 to about 80:20 volume percent, based on the total volume of the mixture and most preferably at about 70:30 volume percent.

In one embodiment herein the mixture of water and water miscible solvent is an azeotropic mixture of water and water miscible alcohol such as the non-limiting example of an azeotropic mixture of water and n-propanol.

In one embodiment herein the solvating of the molten bisphosphate in a mixture of water and water miscible solvent comprises at least 80 percent of the molten bisphosphate being solvated in the mixture, preferably at least 90 percent of the molten bisphosphate being solvated in the mixture, and most preferably at least 95 percent of the molten bisphosphate being solvated in the mixture. In another embodiment, the molten bisphosphate is completely solvated in the mixture of water and water miscible solvent.

In one embodiment of the invention herein the solvating of the molten bisphosphate in the mixture will allow the temperature to be reduced to a temperature of from about 80 degrees to about 90 degrees Celsius, preferably reduced to about 85 degrees Celsius. In one embodiment the water/water miscible solvent mixture is at ambient temperature when contacted with the molten bisphosphate, but can be at any temperature, e.g., from about 25 degrees to about 30 degrees Celsius. The molten bisphosphate can be added to the mixture or vice-versa. The water/solvent mixture can be contacted with the molten bisphosphate over a period of from about 1 minute to about 30 minutes, preferably from about 5 minutes to about 20 minutes and most preferably from about 10 minutes to about 20 minutes, preferably in a drop-wise fashion. In one embodiment the water/solvent mixture can be contacted with the molten bisphosphate in a period of about 15 minutes.

In another embodiment herein of the process the cooling of the solution over a period and to a temperature that provides for crystallization of solid product can be conducted over a period of from about 10 minutes to about 6 hours, preferably from about 1 hour to about 4 hours, more preferably from about 1 hour to about 3 hours, and most preferably from about 2 to about 3 hours.

In one embodiment of the process herein, the cooling of the solution over a period and to a temperature that provides for crystallization of solid product comprises a cooling to a temperature of from about 20 degrees Celsius to about 90 degrees Celsius, preferably from about 25 degrees Celsius to about 75 degrees Celsius, most preferably from about 25 to about 70. It is understood herein that from about 60 to about 80 degrees Celsius, preferably from about 65 to about 75 degrees Celsius is wherein crystallization of product HDP begins to occur. The cooling can be stopped temporarily at the point of crystallization and/or continued to ambient temperature. In one embodiment the cooling is conducted down to ambient temperature. It will be understood that the process step of cooling of the solution over a period and to a temperature that provides for crystallization of solid product can be conducted by cooling to any of the aforementioned temperature ranges over any of the aforementioned periods of time.

In another embodiment herein of the process, the crystallization is carried out at different concentrations of crude bisphosphate in a mixture of water and water miscible solvent.

The crystallization of bisphosphate is performed at a crude bisphosphate/(water-water miscible solvent) weight ratio of from about 1:1.1 to about 1:2, more preferably from about 1:1.2 to about 1:1.75, and most preferably from about 1:1.3 to about 1:1.5. The bisphosphate yield decreased at a ratio higher than of 1:1.5, while at a ratio below 1:1.2 the suspension of the bisphosphate in a mixture of water and water miscible solvent is difficult to stir.

In one embodiment herein the step of increasing the pH of the solution (neutralization) is conducted prior to, and/or during, and/or after the initiation of crystallization, and/or alternatively, the step of increasing the pH of the solution is conducted only after the completion of crystallization. It will be understood herein that the step of increasing the pH of the solution may be conducted at least one of prior to initiation of crystallization, during crystallization, after initiation of crystallization (up until completion of crystallization) and/or after crystallization is complete. It will be understood herein that should the step of increasing the pH of the solution be conducted (in whole or part) after crystallization is complete, then the step of separating the solid product from the solution is conducted only after the step of increasing the pH is complete.

In a preferred embodiment herein, the step of increasing the pH of the solution is conducted before the crystallization or only after crystallization of the product is complete. In one embodiment, it will be understood herein that crystallization of the product is complete when at ambient temperature no further precipitation of product occurs.

The base that can be used herein is any base that will increase the pH as desired, but it can preferably be selected from the group consisting of sodium hydroxide, calcium hydroxide, sodium bicarbonate, sodium carbonate, calcium bicarbonate, potassium hydroxide, potassium carbonate, potassium bicarbonate and combinations thereof. Preferably such a base is a solution of a base such as a 10% solution of sodium hydroxide. In one embodiment the base can comprise two or more of the aforementioned bases.

In one embodiment, the neutralization step of increasing the pH can effectively increase the pH in the process anytime the pH falls below 5.0, or even if the pH falls to as low as 2, to a pH of from about 5.0 to about 8, more preferably from about 5 to about 7.5, and most preferably from about 5 to about 7. In one embodiment a pH of about 5 is most preferred in order to obtain optimal hydrolytic stability although any pH in the recited ranges may be used. Under basic conditions, at pH values of higher than 10 the noticeable hydrolytic decomposition of bisphosphate dissolved takes place. Preferably, the temperature of the mixture following neutralization is from about 70 to about 85, most preferably about 80 degrees Celsius to provide optimal levels of hydrolytic stability, although any temperature in the recited ranges may be used.

The amount of catalyst $MgCl_2$ in the crude bisphosphate may influence the stability of the product after neutralization. The catalyst content in the crude bisphosphate is between 0.02% and 1% w/w, preferably between 0.05% and 0.2%, and most preferably between 0.06% and 0.1%.

The separation of solid product from the solution is conducted by filtration, by means which are generally known in the art. Preferably, the separation of the solid product is complete prior to the next step of the process, i.e. the washing of the separated solid product in the same and/or different mixture of water and water miscible solvent.

The washing of the separated solid product in the same and/or different mixture of water and water miscible solvent can comprise utilizing a recycled mixture of water and water miscible solvent from a previously conducted process of the invention herein, and/or a process step of the process herein, wherein the recycled mixture of water and water miscible solvent can be obtained by distillation, preferably azeotropic distillation of the aqueous waste of such a previously conducted process or process step. Preferably, mixture of water and water miscible solvent is such a same mixture which is recycled from a previous process and/or process step. The process described herein can comprise wherein the mixture of water and water miscible solvent can be recycled for use in subsequent processes, such as wherein the recycled mixture of water and water miscible solvent can be obtained by distillation, e.g., azeotropic distillation.

In one other preferable embodiment the washing of the separated solid product in the same and/or different mixture, is such that the mixture of water and water miscible solvent is a blend of a recycled same mixture from a previous process and/or process step and a different mixture of water and water miscible solvent. In one specific embodiment, the different mixture of water and water miscible solvent comprises water and a different water miscible solvent from that was used previously, or water and the same water miscible solvent as is present in the recycled mixture but when the water miscible solvent is the same, the mixture is new or fresh, i.e., is not provided from a recycled mixture. Still further, in another embodiment, a different mixture of water and water miscible solvent can comprise water and a different water miscible solvent, as well as the same water miscible solvent that was used in a previous process or process step; in such an embodiment either or both of the same and different solvent can be fresh or recycled.

In one specific embodiment the ratio of recycled mixture of water miscible solvent and fresh mixture can be done at any ratio, without a preference to any particular ratio and can be determined by those skilled in the art depending on specific desirable process parameters.

In one embodiment, the step of washing of the solid product which has been washed in the mixture, with water (i.e., the final water wash step), can comprise more than one water wash, preferably at least two water washes. The types of water described above can be used herein and in any other process step herein that utilizes water.

In one embodiment, following the final water wash step, the product can be dried using means which are generally known in the art, to produce a purified bisphosphate. Some such means of drying can comprise for example, at least one of vacuum drying, nitrogen sparging, and argon sparging. $FeCl_3$ can be used herein for removing phosphorous-containing impurities (e.g., phosphorous acids) in manner which is known by those skilled in the art.

The purified bisphosphate can have a purity greater than that of the molten bisphosphate with which the process was initiated, and preferably a purity of at least about 95 percent by weight, preferably at least 98 percent by weight and most preferably at least 99 percent by weight, said percent by weight being based on the weight of the product bisphosphate of the process herein.

In another embodiment the purified bisphosphate has a decreased acidity as compared to the molten bisphosphate with which the process was initiated, preferably, less than about 0.10 mg KOH/g, and more preferably less than about 0.05 mg KOH/g. Such levels of acidity can comprise the substantial absence or the complete absence of acidity.

In yet another embodiment, the purified bisphosphate can have a level of sodium of less than about 50 ppm, preferably less than about 20 ppm and/or a level of magnesium of less than about 50 ppm, preferably less than about 20 ppm and most preferably less than about 10 ppm. Such levels of sodium and/or magnesium can comprise the substantial absence or complete absence of sodium and/or magnesium.

In one embodiment herein the purified bisphosphate made by the process herein has a thermal gravimetric analysis of 1 weight percent loss based on the weight of purified bisphosphate sample tested of from about 290° C. to about 310° C., a thermal gravimetric analysis of 5 weight percent based on the weight of purified bisphosphate sample tested of from about 330° C. to about 350° C., and a thermal gravimetric analysis of 10 weight percent based on the weight of purified bisphosphate sample tested of from about 350° C. to about 370° C.

In one preferable embodiment herein there is provided a plastic comprising the purified bisphosphate, such as the plastics and resins described herein.

In another preferable embodiment there is provided a flame-retardant composition comprising the purified bisphosphate, wherein the purified bisphosphate is one purified by the process herein.

In another embodiment there is provided a plastic comprising the flame-retardant composition. Preferably the plastic is a polycarbonate (PC)/styrenic containing alloy.

The present invention is also directed to resin compositions comprising a flame retardant effective amount of the flame-retardants of formula (I) purified by the process herein and at least one resin (or plastic). The resins used in the compositions of the present invention include but are not limited to styrenic polymers and copolymers, polyphenylene oxide (PPO), acrylonitrile butadiene styrene (ABS), polycarbonate (PC) and mixtures thereof. Specific resins used include PC/ABS mixtures, high impact polystyrene (HIPS) and PPO/HIPS and FR-styrenic composites. These types of resins or polymer mixtures are described for example in U.S. Pat. No. Re. 36,188, U.S. Pat. Nos. 6,727,301 and 6,753,366 the entire contents each of which are incorporated by reference herein. The flame-retarded resin compositions of the present invention are typically useful, for example, in the production of domestic appliances, castings for electrical devices, bedding, furniture and automotive components.

The amount of purified bisphosphate flame retardant typically used in the resin (or plastic) compositions of the present invention generally range from about 2% to about 20%, by weight, of the total weight of the composition, more preferably from about 7% to about 15%, by weight, of the total weight of the composition, with the remainder being resin. The flame retarded resin compositions of the present invention can also include other additives such as antioxidants, stabilizers, fillers as well as other flame retardants. It will be understood that the weight of the other additives can be present in the compositions herein in any desirable or beneficial amount, wherein the above amounts of purified bisphosphate remain the same and the remainder amount being resin, being adjusted downward to reflect the presence of additive, such that the total weight percent is maintained at 100% based on the total weight of the composition.

A preferred flame retarded resin composition of the present invention comprises an effective flame retardant amount of hydroquinone bis(diphenylphosphate), purified by the process herein, having an average value of n of about 1.02 (as present in formula (I)), a polycarbonate and a styrene-containing resin copolymer. A representative polycarbonate that can be used in the compositions of the present invention is Lexan, commercially available from General Electric Company.

EXAMPLES

The following details a non-limiting example of the general purification process herein which comprises crystallization of crude HDP in an azeotropic n-propanol-water solution.

The specific examples below detail a process for the purification of HDP by crystallization in n-propanol-water azeotrope and include recycling of the mother liquor and the aqueous washes, and full recovery of the n-propanol in the form of an azeotrope with water. The process also includes neutralization, i.e., increasing the pH, as described herein. While n-propanol is used herein, one skilled in the art could substitute any water miscible solvent with similar results.

Abbreviations

| | |
|---|---|
| HDP | Hydroquinone bis(diphenyl phosphate) |
| DPCP | Diphenyl chlorophosphate |
| HPLC | High Performance Liquid Chromatography |
| HQ | Hydroquinone |
| TPPO | Triphenyl phosphate |

Example 1

Preparation of Crude HDP: General Procedure

A 500 mL reactor, equipped with a condenser, a thermocouple, an HCl scrubber and a dip tube for $N_2$ purge was charged with DPCP (788 g, 2.93 mole) and $MgCl_2$ (0.5 g). The mixture was stirred and heated to 110° C. HQ (160.3 g, 1.46 mole) was then added to the reaction mixture in one portion and heating continued at this temperature for an additional half an hour. To drive the reaction HCl was removed by $N_2$ purge or by vacuum. The temperature was then raised gradually to 140° C. and the mixture was stirred at this temperature for 7-8 hours. The reaction mixture was then cooled to 120° C. and molten crude HDP was obtained for crystallization in the process herein.

Example 2

Neutralization Before Crystallization: General Procedure

A 500 mL reactor, equipped with a thermocouple, a pH meter electrode, a dropping funnel and a condenser, was charged with 100 g molten crude HDP at 115° C. A solution of 150 g (174 mL) n-propanol-$H_2O$ azeotrope (70:30) was added to the reactor drop wise over 15 minutes allowing the temperature to drop to 85° C. At the beginning of the addition, a stirrable mixture was formed, and then a clear solution was obtained. The solution was cooled to 75-80° C. and a 10% aqueous NaOH solution (2.1 g) was added drop wise to pH 7-8. The solution was then cooled to room temperature with stirring over 2-3 hours. During the cooling, at 65-75° C., the crystallization began, and an exotherm of 2-4° C. was observed.

The pH dropped during the cooling and at room temperature the pH was between 5-6. The solid was washed once with 87 g (100 mL) 70/30 n-propanol/$H_2O$. The solid was then washed twice with 100 g distilled water. A white powder 95.5 g (yield of 95.5%) was obtained after drying under vacuum at 70° C., until a constant weight.

Example 3

Neutralization after Crystallization

A 250 mL four necked flask, equipped with a thermocouple, a pH meter electrode, a dropping funnel and a condenser, was charged with 50 g molten crude HDP at 115° C. A solution of 75 g (87 mL) n-propanol-$H_2O$ azeotrope (70:30) was added to the reactor drop wise over 15 minutes allowing the temperature to drop to 85° C. At the beginning of the addition, a stirrable mixture was formed, and then a clear solution was obtained. The solution was cooled and at about 65° C. the crystallization occurred. The mixture was cooled further to room temperature over 2-3 hours and then a 10% aqueous NaOH solution was added drop wise until a pH of between 6-8 was established. The solid was washed once with 43 g (50 mL) 70/30 n-propanol/$H_2O$ then twice with 50 g distilled water. A white powder, 48.2 g (yield of 96.4%) was obtained after drying under vacuum at 70° C., to constant weight.

The following series of experiments specify the recycling of the mother liquor and aqueous washes

Example 4

Crystallization and Purification of HDP, First Cycle

Crude HDP (90 g) was crystallized in 135 g of 70/30 n-Propanol/$H_2O$ as described in Example 3. Neutralization was done at room (ambient) temperature, to obtain a pH of 7.2, with 1.75 g 10% NaOH. The solid obtained was washed with 90 mL (78 g) 70/30 n-Propanol/$H_2O$, and twice with 90 g deionized (DI) water. The mother liquor and the first wash were mixed to obtain a product solution 1.

Example 5

Crystallization and Purification of HDP, Second Cycle

Crude HDP (90 g) was crystallized in 135 g of the mixed product solution 1 from Example 4. A cloudy solution was obtained at 88° C. Neutralization was done at 30° C., to obtain a pH of 7.8, with 1.75 g 10% NaOH. The first wash was done with a solution consisting of 25 g (~30 mL) of product solution 1 and 60 mL fresh 70/30 n-Propanol/$H_2O$. The first aqueous wash was done with the second aqueous wash of the first cycle, and the second aqueous wash with fresh 90 g DI water. The mother liquor and the first wash were mixed to obtain a product solution 2.

Example 6

Crystallization and Purification of HDP, Third Cycle

Crude HDP (90 g) was crystallized in 135 g of the mixed product solution 2 from Example 5. A cloudy solution was obtained at 88° C. Neutralization was done at 30° C. to obtain a pH of 7.7 with 1.8 g 10% NaOH. The first wash was done with a solution consisting of 25 g (~30 mL) product solution 2 and 60 mL fresh 70/30 n-Propanol/$H_2O$. The first aqueous wash was done with the second aqueous wash of the second cycle, and the second aqueous wash with fresh 90 g DI water. The mother liquor and the first wash were mixed, to obtain a product solution 3.

Example 7

Crystallization and Purification of HDP, Fourth Cycle

Crude HDP (90 g) was crystallized in 135 g of mixed product solution 3 as from Example 6. A cloudy solution was obtained at 88° C. Neutralization was done at 80° C. to obtain a pH of 7.4, with 1.73 g 10% NaOH. The first wash was done with a solution consisting of 25 g (~30 mL) product solution 3 and 60 mL fresh 70/30 n-Propanol/$H_2O$. The first aqueous wash was done with the second aqueous wash of the third cycle, and the second aqueous wash with fresh 90 g DI water. The mother liquor and the first wash were mixed to obtain a product solution 4.

Example 8

Crystallization and Purification of HDP, Fifth Cycle

Crude HDP (90 g) was crystallized in 135 g of mixed product solution 4 from Example 7. A cloudy solution was obtained at 88° C. Neutralization was done at 80° C. to obtain a pH of 7.5 with 1.78 g 10% NaOH. The first wash was done with a solution consisting of 25 g (~30 mL) product solution 4 and 60 mL fresh 70/30 n-Propanol/$H_2O$. The first aqueous wash was done with the second aqueous wash of the fourth cycle, and the second aqueous wash with fresh 90 g deionized water. The mother liquor and the first wash were mixed to obtain a product solution 5.

Example 9

Crystallization and Purification of HDP, Sixth Cycle

Crude HDP (90 g) was crystallized in 135 g solution consisting of 108 g of mixed product solution 5 from Example 8 and 27 g fresh 70/30 n-Propanol/$H_2O$. A cloudy solution was obtained at 88° C. Neutralization was done at 80° C., to obtain a pH of 7, with 1.78 g 10% NaOH. The first wash was done with a solution consisting of 25 g (30 mL) product solution 5 and 60 mL fresh 70/30 n-Propanol/$H_2O$. The first aqueous wash was done with the second aqueous wash of the fifth cycle, and the second aqueous wash with fresh 90 g DI water. The mother liquor and the first wash were mixed to obtain a product solution 6.

The quality of all the products, throughout all six cycles, remained good (see in this regard, Tables 1 and 2).

The products were analyzed by HPLC in the following manner: The samples are prepared volumetrically in acetonitrile and the solution is chromatographed on a short, high efficiency, reverse phase (C-18) column employing a water/acetonitrile gradient, with UV-254 detection. External standardization is performed with separately prepared solutions of phenol, toluene, TPPO, and P2 (high purity product). Area percent normalization is used to quantitate other known components for which no standards are available.

TABLE 1

Yield and composition of the products after recycling (HPLC area %)

| Run | Product | Yield % | P1 | TPPO | P2 | P3 | P4 |
|---|---|---|---|---|---|---|---|
| Ex.ample 4 | Cycle 1 | 96 | — | 0.15 | 99.5 | 0.3 | 0.05 |
| Ex.ample 5 | Cycle 2 | 97.2 | 0.05 | 0.13 | 99.3 | 0.36 | 0.13 |
| Ex.ample 6 | Cycle 3 | 97 | 0.11 | 0.16 | 99.12 | 0.38 | 0.23 |
| Ex.ample 7 | Cycle 4 | 97.3 | 0.18 | 0.15 | 99.1 | 0.37 | 0.2 |
| Ex.ample 8 | Cycle 5 | 97.5 | 0.24 | 0.23 | 98.75 | 0.6 | 0.43 |
| Ex.ample 9 | Cycle 6 | 97.5 | 0.21 | 0.2 | 98.87 | 0.36 | 0.33 |

The HPLC analysis shows a small decrease in the P2% area, and increase in the P1% area after each cycle. P1-P4 are defined below in Scheme 1.

TABLE 2

Analytical results of the products after recycling

| Example | Product | Acid# mg KOH/g | Na ppm | Mg ppm |
|---|---|---|---|---|
| Ex.ample 4 | Cycle 1 | 0.03 | 17 | <3 |
| Ex.ample 5 | Cycle 2 | 0.04 | 19 | <3 |
| Ex.ample 6 | Cycle 3 | 0.05 | 16 | <3 |
| Ex.ample 7 | Cycle 4 | 0.02 | 18 | <3 |
| Ex.ample 8 | Cycle 5 | 0.04 | 30 | 10 |
| Ex.ample 9 | Cycle 6 | 0.03 | 20 | <4 |

Thus, it can be seen that recycling the mother liquor (ML), the organic wash and the aqueous wash leads to products of the invention herein.

Scheme 1: Principal Components of HDP Product

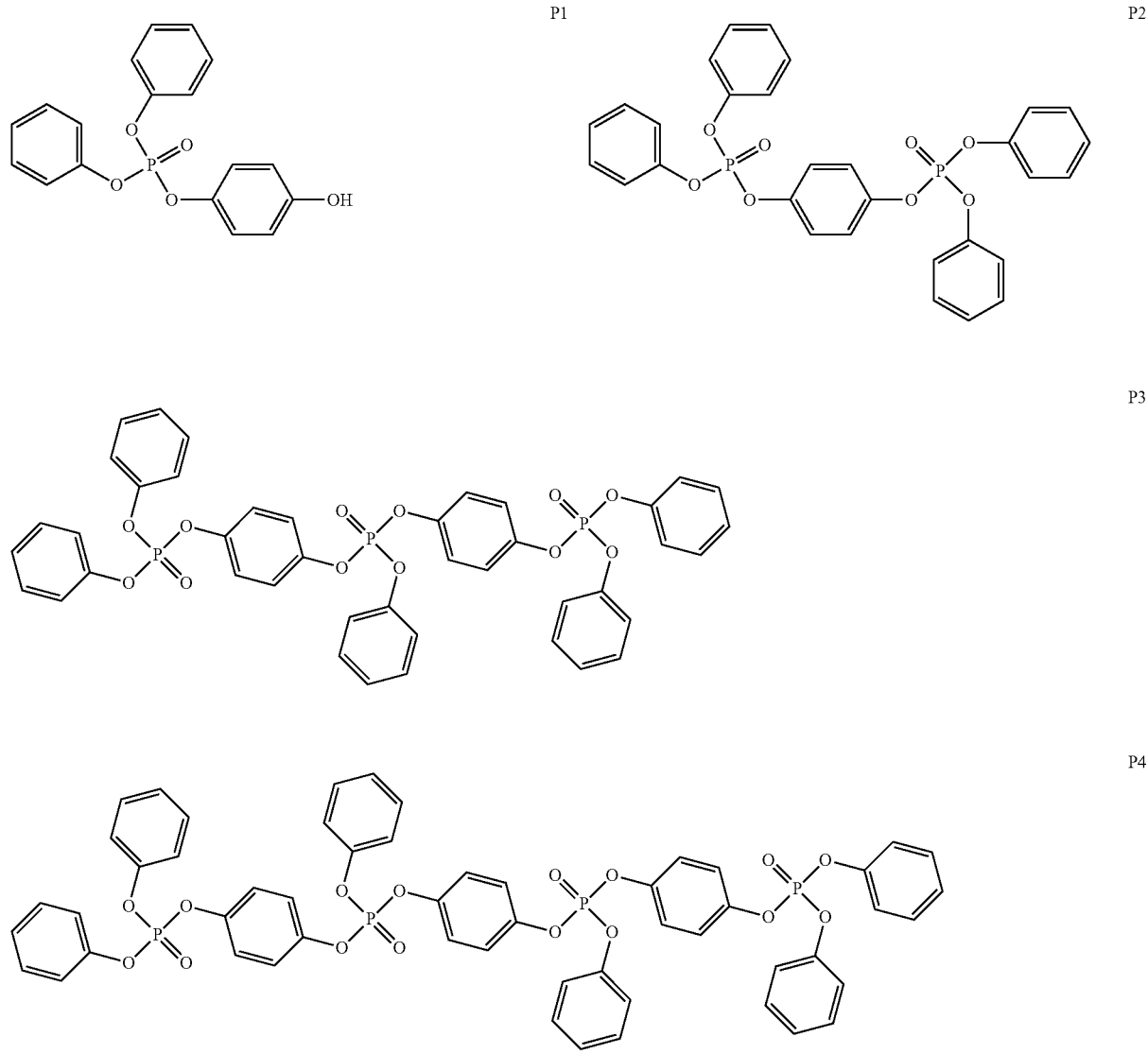

Example 10

Recovery of n-Propanol-Water Azeotrope by Distillation of ML and Aqueous Washes

A combined mixture of all the residual mother liquor and aqueous washes (in all 840 g from Examples 4-9) was distilled at 85° C. and a vacuum of 550 mbar. 366 g of a clear n-propanol-water azeotrope, as distillate was obtained. The distillation residue consisted of two phases: an organic brownish oily phase, phase 1 (6.4 g), at the bottom, and an aqueous upper phase, phase 2 (466 g).

Example 11

Crystallization of HDP with Distilled Recovered n-Propanol-Water Azeotrope

Crude HDP (70 g) was crystallized in 105 g of the distilled n-propanol-water azeotrope distillate from Example 10. Neutralization was done dropwise at 80° C., to obtain a pH of 7, with 1.4 grams of 10% NaOH. A product was obtained in 95% yield and 99.5% purity. All neutralizations herein were done in a drop-wise fashion.

TABLE 3

Yield and composition (HPLC area %) of HDP crystallized with recovered n-propanol azeotrope

| Yield % | P1 | TPPO | P2 | P3 |
|---|---|---|---|---|
| 95 | 0.08 | 0.08 | 99.54 | 0.3 |

TABLE 4

Analyses of HDP crystallized with recovered n-propanol azeotrope

| Acid# mg KOH/g | Na ppm | Mg ppm |
|---|---|---|
| 0.02 | 18 | 3.4 |

Thus, it can be concluded that n-propanol can be easily recovered and used in the crystallization process to give a product of the invention.

Example 12

Thermal Gravimetric Analysis (TGA) was done on the sample from Example 9 according to the method described in Thermogravimetric Analysis of polymers, Scott Kinzy and Robert Falcone in Handbook of Plastics Analysis, Hubert Lobo, Jose V. Bonilla, 2003, which is incorporated herein by reference in its entirety. Further TGA done herein had the following parameters: For the TGA analysis TA Instruments TGA Q500 instrument was used with a 10 mg sample in open Pt pan with ramp 10° C./minute under N2.

The percentages recited in Table 5 are weight percent losses based on the total amount of bisphosphate used in the TGA test.

TABLE 5

Characteristic properties of HDP crystallized in n-propanol azeotrope

| TGA | |
|---|---|
| 1% loss | 301° C. |
| 5% loss | 340° C. |
| 10% loss | 359° C. |

Example 13

Use of Acetonitrile as a Water-Miscible Solvent for Purification

A 250 mL four-neck round-bottom flask, equipped with a pH meter electrode, a condenser and a mechanical stirrer, was charged with 20.2 g crude HDP as prepared in Example 1, and 40 g of a mixture of acetonitrile-water (85:15 w/w). The mixture was heated to 75° C. and a clear solution is obtained. The solution was cooled to 70° C. and 10% aqueous NaOH solution (0.36 g) was added drop-wise to pH 6.8.

The solution was further cooled to room temperature, with stirring, over 2 hours. During the cooling, at ~64° C., the crystallization began. The solid was washed with 20 mL of the acetonitrile-water mixture (85:15 w/w), then twice with 20 g distilled water.

A white powder, 19 g, was obtained after drying under vacuum at 70° C. The final product contained less than 5 ppm Mg, 13 ppm Na and had an acid number of less than 0.05 mg KOH/g.

Comparative Example A

Without Neutralization and without Water Wash

A 250 mL four-neck, round-bottom flask, equipped with a condenser and a mechanical stirrer, was charged with 40 g crude HDP as prepared in Example 1, and 60 g n-propanol. The mixture was heated to 95° C. and a clear solution was obtained. The solution was then cooled to room temperature with stirring over 3 hours. During the cooling, at 58° C., the crystallization began. The solid was washed at room temperature three times with 40 mL n-propanol. The final product in the form of white powder, 38.1 g, was obtained after drying under vacuum at 70° C. The product had an acid number of 0.3 mg KOH/g.

Comparative Example B

With Neutralization but without Water Wash

A 250 mL four-neck, round-bottom flask, equipped with a condenser and a mechanical stirrer, was charged with 40 g crude HDP as prepared in Example 1, and 60 g n-propanol. The solution was cooled to 70° C. and 10% aqueous NaOH (1 g) was added to pH 6.2. The solution was then cooled to room temperature with stirring over 3 hours. During the cooling, at 56° C., the crystallization began. The solid was washed at room temperature three times with 40 mL n-propanol. The final product in the form of white powder, 37.6 g, was obtained after drying under vacuum at 70° C. The product had an acid number of less than 0.05 mg KOH/g, but the Na content was 80 ppm.

The invention claimed is:

1. A process for purifying hydroquinone bis-(diphenylphosphate) comprising:
    solvating molten hydroquinone bis-(diphenylphosphate) in a mixture of water and water miscible solvent at a temperature of at least 30 degrees Celsius or adding solid hydroquinone bis-(diphenylphosphate) to water and a water miscible solvent to a temperature sufficient to solvate the hydroquinone bis-(diphenylphosphate);
    cooling the solution over a period and to a temperature that provides for crystallization of hydroquinone bis-(diphenylphosphate) solid product;
    increasing the pH of the solution prior to, and/or during, and/or after the initiation of crystallization, and/or after crystallization of the product is complete, by the addition of a base; and after crystallization is complete, separating hydroquinone bis-(diphenylphosphate) solid product from the solution;

washing the separated hydroquinone bis-(diphenylphosphate) solid product in the same and/or different mixture of water and water miscible solvent; and, washing the hydroquinone bis-(diphenylphosphate) solid product which has been washed in the mixture of water and water miscible solvent, with water.

2. The process of claim 1 wherein the molten hydroquinone bis-(diphenylphosphate) is first solvated in the water miscible solvent to which water is then added.

3. The process of claim 1 wherein the mixture of water and water miscible solvent is an azeotropic mixture of water and water miscible solvent.

4. The process of claim 1 wherein the step of increasing the pH of the solution is conducted only before the initiation of crystallization.

5. The process of claim 1 wherein the step of increasing the pH of the solution is conducted only after crystallization of the hydroquinone bis-(diphenylphosphate) product is complete.

6. The process of claim 1 wherein the step of increasing the pH of the solution comprises increasing the pH to from about 5 to about 10.

7. A purified hydroquinone bis-(diphenylphosohate) produced by the process of claim 1.

8. A flame-retardant composition comprising the purified bisphosphate of claim 7.

9. A hydroquinone bis-(diphenylphosphate) made by the process of claim 1 wherein the hydroquinone bis-(diphenylphosphate) has an acidity of less than 0.10 mg KOH/g, residual catalyst of less than 50 ppm Mg, and sodium of less than 50 ppm.

10. A hydroquinone bis-(diphenylphosphate) obtained from the process of claim 1 wherein the hydroquinone bis-(diphenylphosphate) has at least one of a melting point higher than 30 degrees C., acidity of less than 0.10 mg KOH/g, residual catalyst of less than 50 ppm Mg, sodium content of less than 50 ppm and,1% weight loss according to TGA of higher than 290 degrees C.

11. The process of claim 1 wherein the water-miscible solvent is a primary alcohol.

* * * * *